United States Patent [19]
Van Lysel et al.

[11] Patent Number: 5,361,761
[45] Date of Patent: Nov. 8, 1994

[54] METHOD AND APPARATUS FOR MEASURING BLOOD IODINE CONCENTRATION

[75] Inventors: Michael S. Van Lysel; Thomas P. Fuerst, both of Madison, Wis.

[73] Assignee: Wisconsin Alumni Research Foundation, Madison, Wis.

[21] Appl. No.: 900,143

[22] Filed: Jun. 17, 1992

[51] Int. Cl.⁵ .......................... A61B 5/14; A61B 6/00; G01N 23/06
[52] U.S. Cl. ................................ 128/653.1; 128/654; 378/53
[58] Field of Search ............ 128/653.1, 654, 632, 128/771; 378/53, 54; 250/370.09, 370.11

[56] References Cited

U.S. PATENT DOCUMENTS

| | | | |
|---|---|---|---|
| 3,822,201 | 7/1974 | Waters | 128/654 |
| 4,024,400 | 5/1977 | Blytas et al. | 378/53 |
| 4,037,585 | 7/1977 | Gildenberg | 128/653.1 |
| 4,432,370 | 2/1984 | Hughes et al. | 128/654 |
| 4,536,790 | 8/1985 | Kruger et al. | 128/654 |
| 4,573,181 | 2/1986 | Grönberg et al. | 378/53 |
| 4,643,891 | 2/1987 | Panek | 128/654 |
| 4,887,604 | 12/1989 | Shafer et al. | 128/654 |
| 5,078,135 | 1/1992 | Caprioli | 128/632 |

FOREIGN PATENT DOCUMENTS 2083908  3/1982  United Kingdom ............... 378/53

*Primary Examiner*—K. M. Pfaffle
*Attorney, Agent, or Firm*—Andrus, Sceales, Starke & Sawall

[57] ABSTRACT

A method and apparatus for measuring blood iodine concentration draws a continuous specimen of blood containing iodine from the left ventricle of the heart and exposes that specimen to a source of X-rays. The attenuated level of X-rays passing through the specimen is compared with the unobstructed level of X-rays to determine the concentration of iodine in the blood. The measurement is then corrected to account for the effects of dispersion caused by the travel of the specimen from the heart to the measurement zone.

14 Claims, 2 Drawing Sheets

METHOD AND APPARATUS FOR MEASURING BLOOD IODINE CONCENTRATION

BACKGROUND OF THE INVENTION

The present invention relates to cardiac angiography and more specifically to a method and apparatus for determining the concentration of the iodinated contrast agent in the blood.

Cardiac angiography is an important diagnostic tool, providing high spatial and temporal resolution images of the coronary arteries and cardiac chambers. Angiography is often the definitive test regarding the status of a patient's cardiac anatomy and function. However, one disadvantage of angiography is the projection nature of the images obtained. As a consequence, estimation of the volume of the left ventricle (LV) from angiographic images relies upon a geometric model of the left ventricular chamber. While this technique has been shown to provide accurate LV volumes in many cases, it has also been shown that cardiac disease and dysfunction can result in the LV shape deviating from the assumed shape, resulting in an inaccurate measurement of LV volume. Measurement of left ventricular volume provides important prognostic information regarding several cardiac disease states. It would be desirable to have a technique which provides the LV volume without recourse to an assumption regarding its shape.

Densitometric analysis of digital subtraction angiography (DSA) images can, theoretically, provide such a measurement of LV volume. Ideally, the value of a pixel in a DSA image is given by $$D = \mu \rho t$$

where $\mu$ is the iodine attenuation coefficient, $\rho$ is the blood iodine concentration, and t is the thickness of the iodine containing vascular structure at the position of the pixel. One of the problems encountered in making this measurement is the inability to know $\rho$, the concentration of the iodinated contrast agent in the blood.

It is an object of the present invention to provide a method and apparatus for determining the concentration of iodine in the blood in order to provide an accurate measurement of left ventricle volume.

SUMMARY OF THE INVENTION

A method and apparatus for determining the blood iodine concentration utilizes a cardiac catheterization procedure that gives access to the blood in the left ventricle of the heart via a catheter placed in the heart.

In accordance with one aspect of the invention, a blood specimen is continuously withdrawn from the left ventricle through a catheter as the iodine bolus passes through the ventricle. In order to provide adequate mixing of blood and iodine, the contrast agent is injected into the right heart side of the circulation.

In accordance with another aspect of the invention, the blood specimen is then exposed to a source of X-rays and the attenuated level of X-rays passing through the specimen is measured.

In accordance with yet another aspect of the invention, the X-ray source output is also simultaneously measured, after passing through a water filled catheter of equal diameter to the withdrawal catheter, and the two levels are then compared to obtain an iodine concentration level.

In accordance with yet another aspect of the invention, the measured blood iodine concentration level is corrected to account for the effects of dispersion caused by withdrawal of the specimen from the heart, through the connecting tubing, to the detection cell.

The present invention thus provides a method and apparatus for accurately measuring the iodine concentration level in the blood as a function of time during cardiac angiography.

The device and method can also be used to measure the blood iodine concentration in any case where sufficient mixing of blood and iodine has occurred between the site of injection and site of withdrawal.

BRIEF DESCRIPTION OF THE DRAWINGS

The drawings illustrate the best mode presently contemplated of carrying out the invention.

In the drawings.

DETAILED DESCRIPTION OF THE INVENTION

Figure 1:
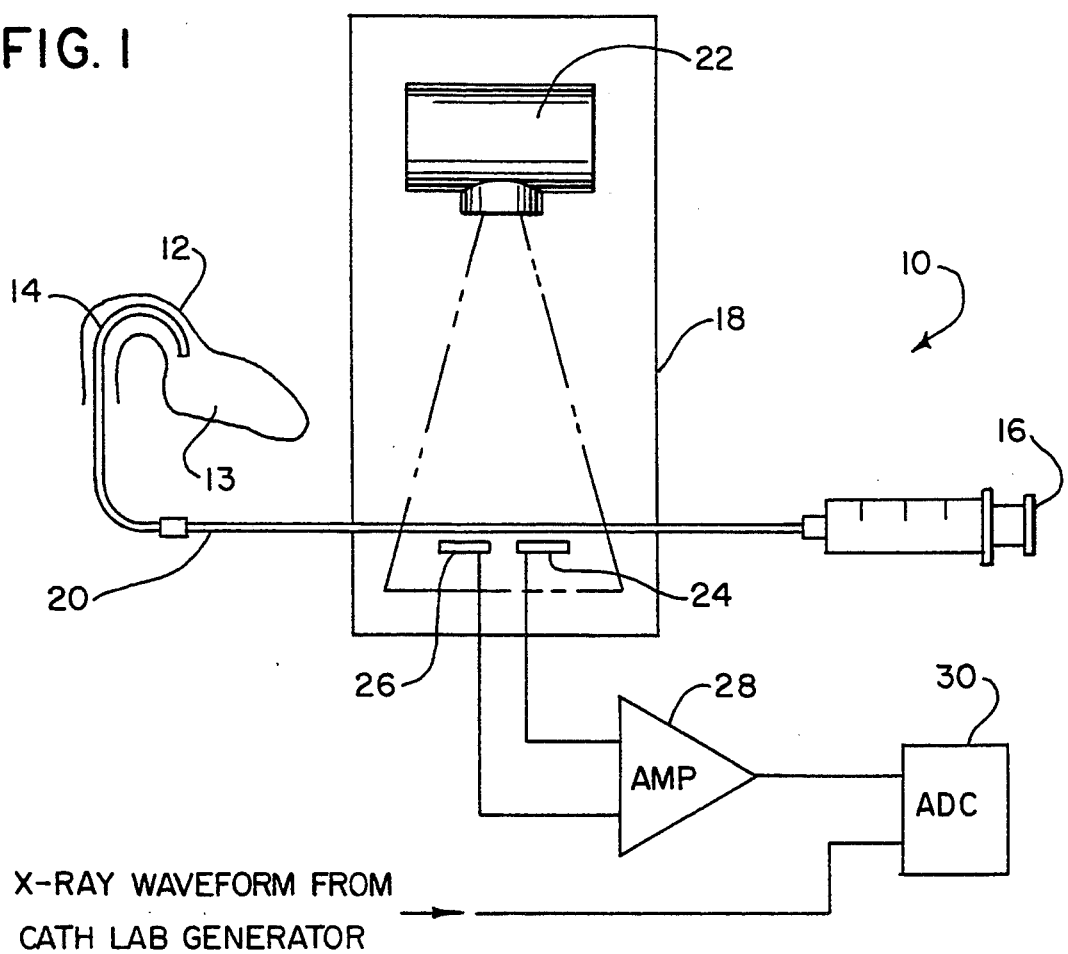
FIG. 1 is a schematic of an apparatus constructed according to the present invention and utilized to carry out the method of the present invention.
Figure 3:
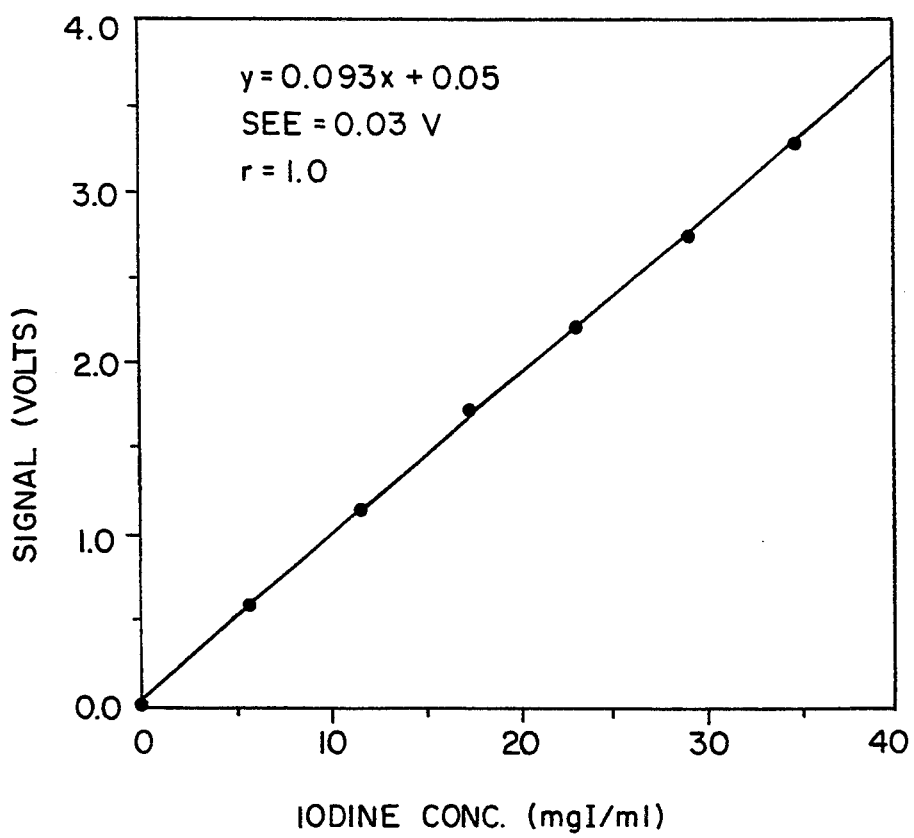
FIG. 3 is a calibration graph showing the measured relationship between the output signal voltage and the iodine concentration.

FIG. 1 illustrates an iodine detection system 10 utilized to carry out the method of the invention. Utilizing this system and standard catheterization procedures, blood is withdrawn at a constant rate from the ascending aorta 12 or the left ventricle 13 through a catheter 14 using a withdrawal pump 16. The withdrawal rate is typically 30 ml/min and lasts between 30–40 sec. Catheter 14 is connected to detection cell 18 by means of 130 cm of additional extension tubing 20 (internal diameter of 0.06"). Within cell 18 tubing 20 passes between a constant potential X-ray source 22 (MicroFocus Imaging, Hammond, Ind.) operated at 45 kV and 3 mA and a 30.0×3.4 mm PIN photodiode 24. Photodiode 24 generates an electrical current in response to the X-rays. A second photodiode 26 lies beside the first one and serves as a reference detector to correct for output fluctuations in source 22. The signals generated by the two detectors 24 and 26 are amplified, subtracted and filtered by operational amplifier 28 whose output signal is proportional to the difference between the two signals generated by detectors 24 and 26. Thus, the concentration of iodine in the blood is determined by measurement of the X-ray attenuation. The nature of X-ray attenuation requires that the signals generated by detectors 24 and 26 be logarithmically amplified before subtraction in order to obtain a signal linear with iodine concentration. However, when the amount of attenuation is small a sufficiently linear signal will result even without logarithmic amplification. This latter case holds for iodine concentrations encountered after venous injection of radiographic contrast medium. FIG. 3 shows the measured relationship between the output signal of the iodine detection system using linear amplification for an iodine concentration range of 0 to 35 mgI/ml. The signal generated by the operational amplifier is transmitted to analog-to-digital converter (ADC) 30 which digitizes the signal. A second channel of the ADC records the X-ray pulses of the catheterization laboratory's imaging system in order to allow subsequent registration of the iodine-concentration-curve and the simultaneously acquired image data.

Figure 2:
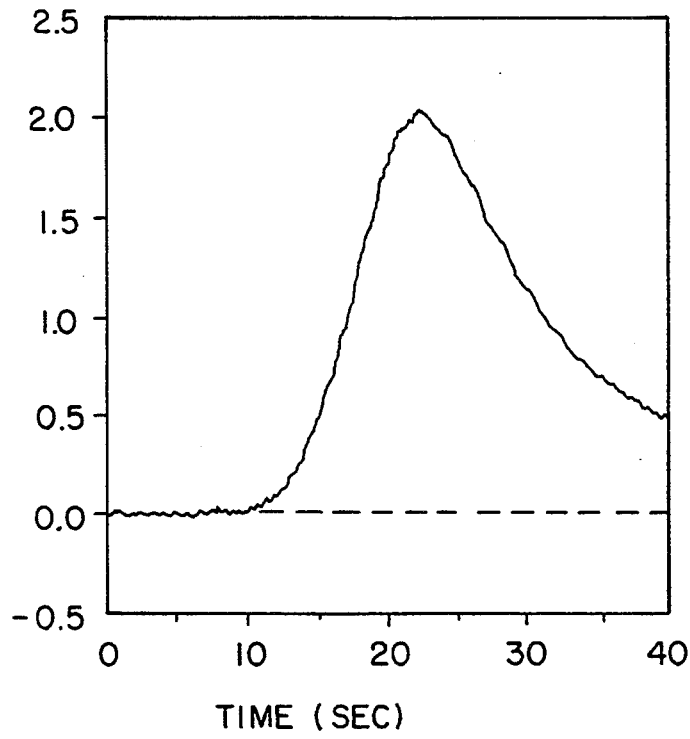
FIG. 2 is a graph showing the amplified difference signal between the iodine and reference detectors as a function of time.

FIG. 2 is a graph showing the difference signal between detectors 24 and 26 due to the changing iodine concentration versus the total time of the withdrawal process. However, since the measurement zone, i.e. measurement cell 18, is located some distance from the left ventricle and it is the purpose of the system to determine the blood iodine concentration at the tip of the catheter at each instant in time, it is necessary to correct the measured signal for errors caused by the dispersion of the iodine concentration curve during passage of the specimen from the left ventricle to measurement zone 18. The technique employed herein was the deconvolution of the measured system transfer function from the raw recorded signal.

To test the accuracy of the correction process, the concentration-time curve of the bolus was recorded as it entered sampling system 10. This is called the TRUE signal. A signal from the same bolus was recorded after it had traversed sampling system 10. This signal, which is the TRUE signal acted upon by the system transfer function, is called the MEASURED signal. Application of the deconvolution process to this MEASURED signal yields the CORRECTED signal, which should resemble the TRUE signal.

Figure 4:
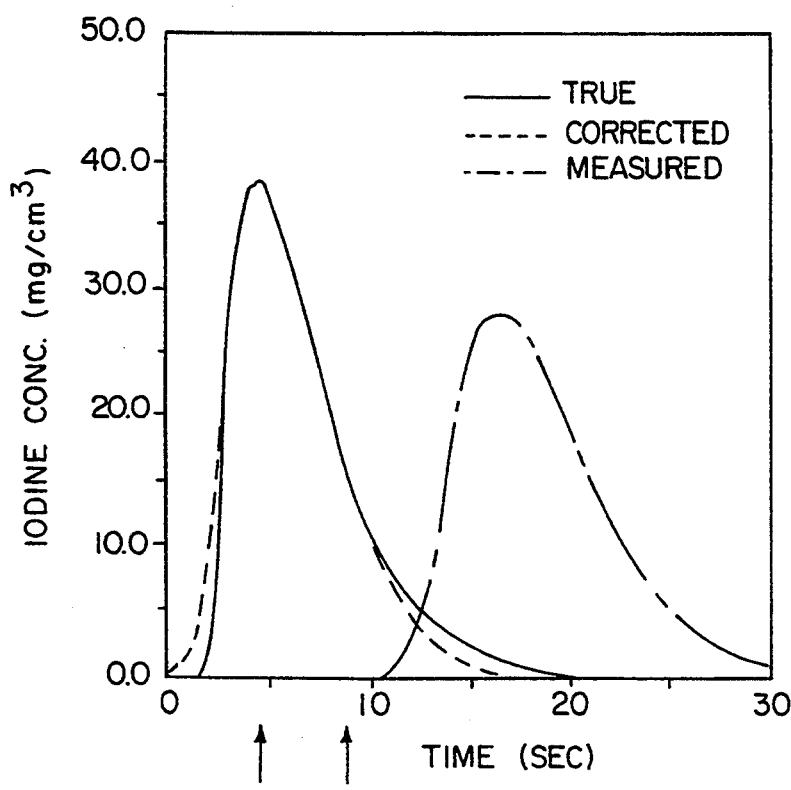
FIG. 4 is a graph showing the measured iodine concentration, the corrected iodine concentration and the true iodine concentration as a function of time.

FIG. 4 shows an example of the TRUE, MEASURED and CORRECTED signals. The rms error of all signals was measured to be less than 4% across the region of the contrast-pass-curve (CPC) where videodensitometric analysis of the image data will be performed. This region, marked by arrows in FIG. 4, extends from the peak of the CPC to the point where the concentration falls to one half the peak value. FIG. 4 also shows that the TRUE and CORRECTED signals diverge in the early and late portions of the CPC. This behavior is likely due to errors in the extrapolation of the tail of the TRUE signal and the leading edge of the MEASURED signal (and consequently the leading edge of the CORRECTED signal) are sensitive to this extrapolation. Thus deviations of the two signals in this experiment may be artifactual, due to the experimental design. Since the deviations affect regions of the curve which are not used for videodensitometric quantitation of image data, they are not of great concern.

The present invention thus provides a method and apparatus for accurately measuring the concentration of iodine in the blood. One application for this measurement is the measurement of left ventricular volume using digital subtraction angiography.

Various modes of carrying out the invention are contemplated as being within the scope of the following claims particularly pointing out and distinctly claiming the subject matter regarded as the invention.

I claim:

1. An apparatus for measuring blood iodine concentration comprising:
   withdrawal means for obtaining a specimen of blood containing iodine,
   a source of radiation,
   conduit means for passing said specimen through said radiation,
   means for detecting a specimen level of radiation passing through said specimen,
   means for detecting a source level of radiation emitted by said radiation source,
   means for comparing said specimen level to said source level and generating a difference signal representing a measurement of the blood iodine concentration, and
   means for correcting said difference signal for effects of dispersion within said withdrawal means.

2. The apparatus defined in claim 1 wherein said withdrawal means comprises a withdrawal pump and catheter connected to the left ventricle of the heart.

3. The apparatus defined in claim 1 wherein said means for detecting the level of radiation passing through said specimen comprises a first photodiode exposed to said radiation, with said conduit means passing said specimen between said radiation source and said first photodiode.

4. The apparatus defined in claim 3 wherein said means for detecting the level of radiation emitted by said radiation source comprises a second photodiode disposed substantially adjacent said first photodiode and exposed to said radiation.

5. The apparatus defined in claim 4 wherein each of said first and second photodiodes generate a signal in response to the detection of radiation and said means for comparing further comprises signal processing circuitry connected to said first and second photodiodes with said circuitry generating said difference signal generated by said first and second photodiodes.

6. The apparatus defined in claim 1 wherein said source of radiation comprises means for generating X-rays.

7. An apparatus for measuring the blood iodine concentration of a blood specimen drawn from the left ventricle of the heart, said apparatus comprising:
   a withdrawal means including a pump and catheter connected to the left ventricle of the heart to obtain a specimen of blood containing iodine,
   an X-ray source to provide a beam of X-rays,
   conduit means for passing said specimen through said beam of X-rays,
   a first photodiode disposed in the beam of said X-rays and with said conduit means passing said specimen between said X-ray source and said first photodiode so that said first photodiode detects a specimen level of X-ray radiation,
   a second photodiode disposed substantially adjacent said first photodiode and in the beam of said X-rays so that said second photodiode detects a source level of X-ray radiation, with said source level being higher than said specimen level,
   means for comparing said specimen level to said source level and generating a difference signal representing a measurement of blood iodine concentration and
   means for correcting said difference signal for the effects of dispersion within said withdrawal means.

8. The apparatus defined in claim 7 further comprising an operational amplifier connected to said first and second photodiodes whereby an output signal of said operational amplifier is proportional to the difference signal generated by said means for comparing.

9. A method of measuring blood iodine concentration, as a function of time, following the injection of an iodinated contrast agent into the vascular system comprising the steps of:
   withdrawing a specimen of blood at a withdrawal site, through a withdrawal system for an extended period of time, during the period of time that iodinated blood is flowing past the withdrawal site, exposing said specimen to a source of radiation, detecting a specimen level of radiation passing through said specimen, detecting a source reference level of radiation, measuring the blood iodine concentration by logarithmically subtracting said specimen level from said reference level to obtain a difference signal, correcting said difference signal for the effects of dispersion within said withdrawal system.

10. The method of measuring blood iodine concentration defined in claim 9 wherein said step of exposing said specimen to a source of radiation comprises exposing said specimen to a source of X-rays.

11. The method of measuring blood iodine concentration defined in claim 9 wherein the specimen withdrawing step comprises drawing blood from the left ventricle of the heart with a withdrawal pump connected to a catheter inserted into the left ventricle.

12. The method of measuring blood iodine concentration defined in claim 9 wherein the exposing of the specimen and detecting of the specimen level steps comprise passing said specimen between an X-ray source and a first photodiode.

13. The method of measuring blood iodine concentration defined in claim 12 wherein said detecting the reference level step comprises exposing a second photodiode to said X-ray source.

14. The method of measuring blood iodine concentration defined in claim 13 wherein said measuring step comprises transmitting signals generated by said first and second photodiodes to an operational amplifier.

* * * * *

UNITED STATES PATENT AND TRADEMARK OFFICE
CERTIFICATE OF CORRECTION

PATENT NO. : 5,361,761
DATED : 11/8/94
INVENTOR(S) : Michael S. Van Lysel; Thomas B. Fuerst It is certified that error appears in the above-indentified patent and that said Letters Patent is hereby corrected as shown below:

Column 1, line 4, after the title insert the following:

--- This invention was made with United States Government support awarded by the National Institutes of Health (NIH), Grant No. DK-14881. The United States Government has certain rights in this invention. ---

Signed and Sealed this

Eighteenth Day of April, 1995

BRUCE LEHMAN

*Attest:*

*Attesting Officer*

Commissioner of Patents and Trademarks